United States Patent [19]
Fell et al.

[11] Patent Number: 5,360,504
[45] Date of Patent: Nov. 1, 1994

[54] METHOD OF BONDING AN ADHESIVE TO FOAM

[75] Inventors: Joseph P. Fell; Richard D. Schulz; Mary J. Meyer, all of Neenah; Allan J. Krueger, Winneconne; Franklin M. C. Chen; Yung H. Huang, both of Appleton, all of Wis.

[73] Assignee: Kimberly-Clark Corporation, Neenah, Wis.

[21] Appl. No.: 55,052

[22] Filed: Apr. 28, 1993

[51] Int. Cl.$^5$ .................................. B32B 31/00
[52] U.S. Cl. ............................ 156/247; 156/78; 156/79; 156/247; 264/321
[58] Field of Search ............... 156/247, 78, 79; 264/321; 428/284, 245, 314.4, 314.5; 604/369, 904

[56] References Cited

U.S. PATENT DOCUMENTS

| | | | |
|---|---|---|---|
| 3,669,786 | 2/1970 | Moore | 156/78 X |
| 3,881,490 | 5/1975 | Whitehead et al. | 128/287 |
| 3,887,408 | 6/1975 | Hoey | 156/247 X |
| 3,901,240 | 8/1975 | Hoey | 156/78 X |
| 3,906,137 | 9/1975 | Bauer | 428/315 X |
| 3,954,537 | 5/1976 | Alfter | 156/82 |
| 4,000,028 | 12/1976 | Hoey | 156/79 |
| 4,069,822 | 1/1978 | Buell | 128/294 |
| 4,100,324 | 7/1978 | Anderson et al. | 428/288 |
| 4,182,649 | 1/1980 | Isgur | 162/101 X |
| 4,196,254 | 4/1980 | Puskadi | 428/341 |
| 4,341,209 | 7/1982 | Schaar | 128/156 |
| 4,353,762 | 10/1982 | Bouda | 156/64 X |
| 4,358,489 | 11/1982 | Green | 428/31 |
| 4,359,357 | 11/1982 | Friese | 156/201 |
| 4,397,644 | 8/1983 | Matthews et al. | 604/378 |
| 4,470,857 | 9/1984 | Casalou | 156/66 X |
| 4,484,574 | 11/1984 | DeRusha et al. | 128/156 |
| 4,547,243 | 10/1985 | Brody | 156/64 |
| 4,554,191 | 11/1985 | Korpman | 428/35 |
| 4,554,193 | 11/1985 | Erickson | 428/40 |
| 4,573,986 | 3/1986 | Minetola | 604/366 |
| 4,623,340 | 11/1986 | Luceri | 604/385 R |
| 4,627,847 | 12/1986 | Puletti et al. | 604/366 |
| 4,656,074 | 4/1987 | Conley | 428/95 |
| 4,692,161 | 9/1987 | Puletti et al. | 604/366 |
| 4,704,107 | 11/1987 | Coates | 604/357 |
| 4,718,898 | 1/1988 | Puletti et al. | 604/366 |
| 4,731,066 | 3/1988 | Korpman | 604/366 |
| 4,781,710 | 11/1988 | Megison et al. | 604/378 |
| 4,844,965 | 7/1989 | Foxman | 428/91 |
| 4,872,870 | 10/1989 | Jackson | 604/366 |
| 4,904,249 | 2/1990 | Miller et al. | 604/378 |
| 4,908,026 | 3/1990 | Sukiennik et al. | 604/378 |
| 4,961,982 | 10/1990 | Taylor | 428/41 |
| 5,021,257 | 6/1991 | Foster et al. | 427/2 |
| 5,064,492 | 11/1991 | Friesch | 156/191 |
| 5,089,535 | 2/1992 | Malwitz | 521/141 X |
| 5,091,240 | 2/1992 | Kajander et al. | 428/198 |
| 5,098,500 | 3/1992 | Reed | 156/253 X |
| 5,197,959 | 3/1993 | Buell | 604/385.1 |
| 5,208,266 | 5/1993 | Yamazaki | 521/79 X |

FOREIGN PATENT DOCUMENTS

0025315A1  8/1980  European Pat. Off. .

*Primary Examiner*—David A. Simmons
*Assistant Examiner*—Charles Rainwater
*Attorney, Agent, or Firm*—Mark L. Davis

[57] ABSTRACT

A method is provided for bonding an adhesive to a polyolefin foam, and preferably a non-crosslinked polyethylene foam. The foam is useful as a liquid-impervious backing in a disposable absorbent article, such as a panty liner, a sanitary napkin, a diaper, a adult incontinent garment, a training pant, and the like. The adhesive is applied to a substrate which is then brought into intimate contact with one side of the foam's surface. Optionally, heat and pressure may be applied to enhance bonding.

23 Claims, 1 Drawing Sheet

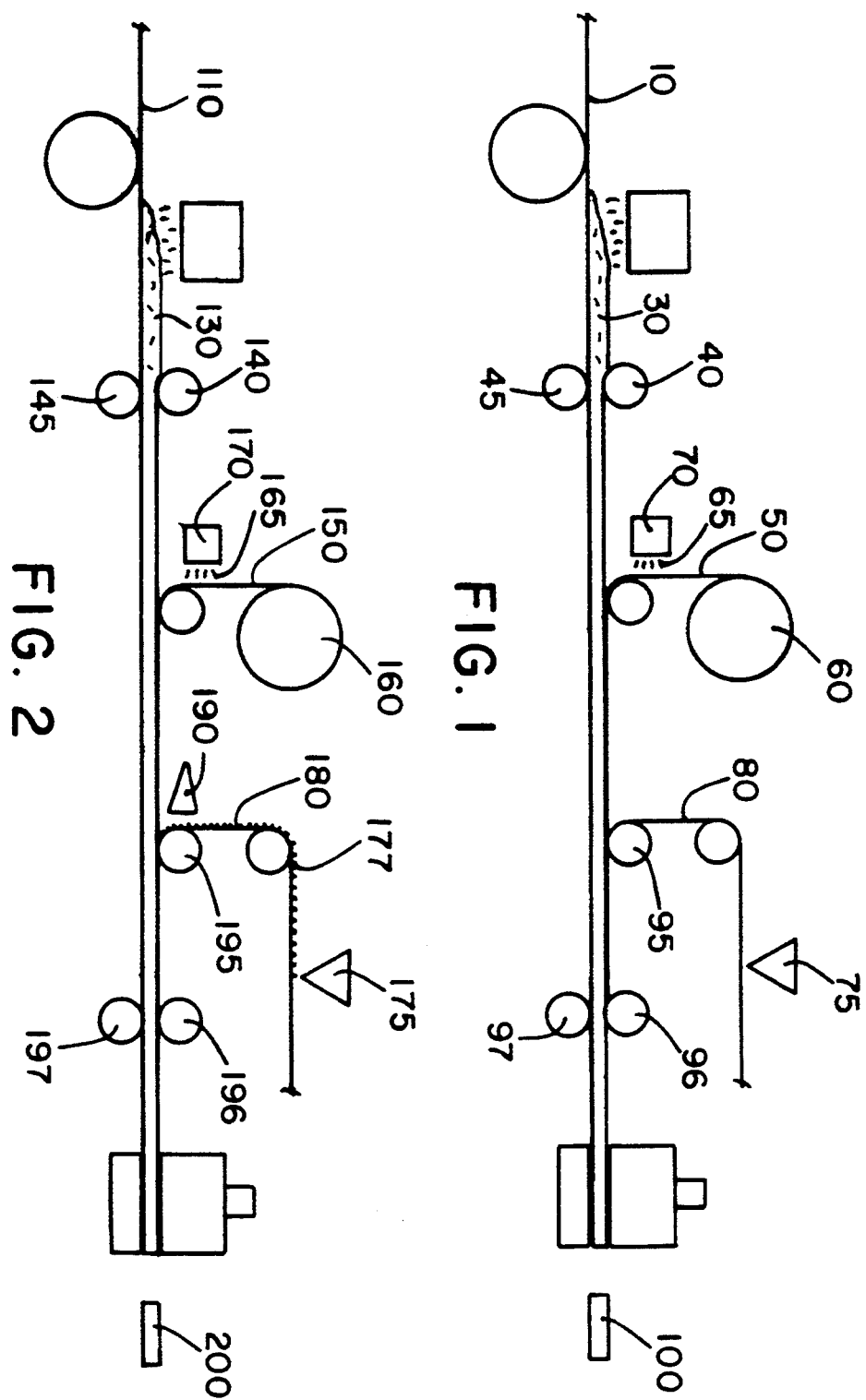

METHOD OF BONDING AN ADHESIVE TO FOAM

FIELD OF THE INVENTION

This invention relates to a method of applying a pressure-sensitive adhesive to a foam. Particularly, the invention relates to a method of applying a garment attachment type adhesive to a non-crosslinked polyolefin foam that may be used as a liquid-impermeable backing member for disposable absorbent articles.

BACKGROUND OF THE INVENTION

Disposable garments such as diapers, training pants, sanitary napkins, panty liners, and incontinent garments, and especially catamenial devices have been undergoing considerable modification which have reduced their thickness but has retained or improved their absorbency and ability to retain body exudates. For convenience in the description, a panty liner or a very thin absorbent pad used primarily for feminine hygiene which may be used for undergarment protection between menstrual periods as well as absorbing light flow between and during periods will be described herein.

Generally, a panty liner comprises: a liquid-pervious, body side cover which is comfortable to the wearer; an absorbent core, typically composed of a fibrous material capable of absorbing body exudates and which may be a natural or a synthetic material or a combination of both; and a liquid-impervious baffle. The baffle's periphery may be coincident with the cover and the absorbent core, but this is not required.

Usually, the backing is a polyethylene film having a thickness of about 0.001 to about 0.005 of an inch (0.025 to 0.13 millimeters). The construction of a panty liner generally provides for a pressure sensitive adhesive applied to the garment facing side of the baffle. The adhesive is of the type that is capable of securing the panty liner to the crotch portion of an undergarment, yet permitting removal of the panty liner when soiled. In applying a pressure-sensitive adhesive to the liquid-impermeable baffle, a common practice is to transfer coat the adhesive on a suitable substrate, such as a Kraft paper that is silicone coated.

A panty liner's thinness makes it very flexible, which allows the panty liner to wrinkle during use and fold at the line along the edges as the panty liner is arcuately bent. When the panty liner's entire periphery is compressed or compacted sufficiently to seal the edges, relatively harsh and sharp edges are formed which tend to be abrasive. In attempting to obviate this undesirable abrasive edge, foamed materials have been utilized as a baffle to form a softer edge. A difficulty arises in producing a panty liner that is both low in cost to manufacture and comfortable to the wearer. For the panty liner to be cost competitive, the foam must be thin but at the same time have a structural integrity to withstand the forces applied to the adhesive coated surface when the panty liner is removed or repositioned.

Polyolefin foams, and specifically a polyethylene foam, have a low surface energy rendering it difficult to obtain a good bonding of a garment adhesive to the foam material. The prior art describes a number of methods that have attempted to increase the bonding of adhesives to polyolefin surfaces. These techniques are time consuming, costly and generally ineffective for constructing panty liners. It must also be borne in mind that the garment adhesive is in a hot melt state and cannot be directly applied to the foam because the foam is far too heat sensitive.

In one method disclosed in the patent literature for applying a garment adhesive to a polyethylene foam the adhesive is mixed in a hydrocarbon carrier prior to its application on the foam. This method is impractical for products that intimately contact human skin because the hydrocarbon may cause skin irritations or other health risks. Additionally, using solvents as a carrier for applying adhesive requires massive ovens for removing the solvents, adding to the product's cost.

Other methods disclosed in the prior art have concentrated on improving the foam's surface characteristics, making it more receptive to adhesive bonding. These methods include corona or flame treatment of the foam prior to its contacting the adhesive and/or using various adhesive primers to enhance the bond.

Yet another method disclosed in the patent literature uses a double-faced pressure sensitive adhesive tape for securing a polyethylene foam backing to the clothing of a user. The tape has an adhesive coating applied to each surface. The adhesive level of the double-faced tape attached to the undergarment is less than the adhesive level of the side of the double-faced tape attached to the ethylene polymer containment backing. The literature also teaches that if the formulation of the adhesive is the same on both sides of the double-faced tape, when the release strip is removed it delaminates the adhesive from the foam backing, pulling the adhesive completely away from the foam rather than being completely released.

While the above methods have had limited success in their application with crosslinked polyolefin foams, it has been found that these methods are unsatisfactory for bonding an adhesive to a non-crosslinked polyethylene foam.

It is therefore desireable to transfer coat a substrate with an adhesive without having to cure the adhesive using ovens. It is also desirable to coat a garment adhesive onto a suitable substrate and then transfer coat the adhesive from the substrate to a polyolefin foam, and preferably a non-crosslinked foam, without having to pre-treat the foam surface using a corona or flame treatment or other surface modifiers.

SUMMARY OF THE INVENTION

Briefly, the present invention relates to a method for applying an adhesive to an absorbent article adapted to be removably attached to an undergarment. The article can include a liquid-impervious polyolefin foam backing member having a garment facing side and a body facing side. A garment adhesive is applied to the garment facing side of the backing member by transfer coating the adhesive onto a suitable substrate. The adhesive is covered by a releasable peel strip that protects the adhesive from prematurely adhering to itself, other objects, or from becoming contaminated.

In its broadest embodiment, the method comprises the steps of applying an adhesive to a surface of a substrate; and contacting a polyolefin foam to the adhesive side of the substrate. In this embodiment it is preferred that the foam contain an amount of aging modifier, as measured by the amount of extractable oxygen using Electron Spectroscopy for Chemical Analysis (hereinafter ESCA and described in greater detail below), of less than about 3%, and preferably less than 1%. The adhesive can have a viscosity of less than about $8 \times 10^8$ centipoise and still bond to the surface of the foam.

Another embodiment of the invention comprises applying an adhesive to a surface of a substrate; contacting a polyolefin foam to the substrate's adhesive side; and heating the adhesive to a temperature ranging from about 140° F. (60° C.) to about 330° F. (165.5° C.). Preferably the adhesive is heated to a temperature ranging from about 160° F. (71° C.) to about 330° F. (165.5° C.).

The general object of the present invention is to provide for a method of transferring an adhesive from a substrate to a polyolefin foam. A more specific object of this invention is to provide a method for producing an absorbent article which has a liquid-impervious backing comprising a polyolefin foam and a garment adhesive bonded to a surface of the foam which lies adjacent to the undergarment.

Another object of this invention is to provide a method of transfer coating an adhesive onto a polyolefin foam so that on removal of the peel strip from the panty liner, the adhesive will not delaminate from the foam.

Another object of this invention is to provide a method for bonding an adhesive to a non-crosslinked polyethylene foam.

These and other objects of the invention will become apparent to those of ordinary skill in the art upon a study of the following specification and appended claims.

BRIEF DESCRIPTION OF THE DRAWINGS

FIG. 1 is a schematic of the method where adhesive is bonded to foam without the use of heat.

FIG. 2 is a schematic of the method where adhesive is bonded to foam using heat.

DETAILED DESCRIPTION OF THE PREFERRED EMBODIMENTS

While the invention will be described in connection with certain preferred embodiments, i.e. bonding a pressure sensitive adhesive to a panty liner, it is to be understood that the invention is not to be limited to a panty liner. For example, the invention may be used in the production of diapers, training pants, incontinent garments, sanitary napkins, and the like.

Turning now to the drawings and referring first to FIG. 1, an assembly line for producing a panty liner incorporating this invention is shown. A liquid-pervious cover 10 has a thin, uniform layer of absorbent 30 airlaid onto one surface thereof. The cover 10 and the absorbent 30 are pressed between two rollers 40 and 45 to densify the absorbent 30. Optionally, the rollers 40 and 45 may supply sufficient pressure, and heat if required, to hydrogen bond the cover 10 to the absorbent 30 as well as to emboss a pattern thereon. A foam 50 is unwound from supply roll 60 and sprayed with a hot melt construction adhesive 65 from sprayer 70. The foam 50 is applied to the absorbent 30. An applicator 75 applies a garment adhesive onto one surface of peel strip 80. Although not required, bonding of a garment adhesive to the foam 50 may be enhanced by applying pressure from one or more compression rollers 95, 96 and 97. After bonding, a panty liner 100 is die cut from the laminated material comprising the cover 10, the absorbent 30, the foam 50, a garment adhesive, and peel strip 80.

The term "bonded" we mean that the attractive force of the garment adhesive to the surface of the foam is sufficiently strong so that the foam's coated surface will be compromised, i.e. tear, before more than 30% of the garment adhesive delaminates from the foam's coated surface area.

The material forming the liquid-pervious cover 10 may be any suitable material that is pervious to liquids and nonirritating. For example, the material may be carded webs of polyester, polypropylene, nylon or other heat bondable fibers. Other materials that may be suitable are net materials or finely perforated film webs. A particularly preferred material is spunbond polypropylene fabric. The most preferred spunbond polypropylene webs have a basis weight of from about 10 to about 40 gsm. A spunbond material containing a whitener such as titanium dioxide ($TiO_2$) or calcium carbonate ($CaCO_2$) is desirable because the color exhibits good stain masking properties to hide body liquid that has permeated into the absorbent core. Spunbond also has sufficient strength that the cover does not tear or fall apart in use.

The absorbent 30 may be any desired material. Typical of such materials are rayon, polyesters, coforms and combination of these absorbent fibers. A preferred material is a wood fiber fluff as it is low in cost. The fluff can contain, either as a separate layer or mixed with the fluff, cross-linked, highly absorbent polymers ordinarily referred to as superabsorbents.

It is critical in this embodiment of this invention, i.e. for a garment adhesive to bond to the foam 50 without applying heat to the garment adhesive, the foam have an amount of aging modifier of less than about 3%, preferably less than about 1%, and most preferably less than about 0.5%. For the purpose of this invention, the amount of aging modifier is determined by measuring the amount of extractable oxygen in the foam 50. The amount of extractable oxygen is determined by performing Electron Spectroscopy for Chemical Analysis (hereinafter ESCA) on the foam 50. The foam 50 was subjected to standard ultra-high vacuum procedures during preparation and introduction into an analytical chamber. All spectra were collected on a Surface Science Instrument SSX-100 ESCA Spectrometer equipped with a monochromatic Al $K_\alpha$-ray source. Initial ESCA survey scans were measured from foam 50 samples to determine amounts of oxygen present. The samples were subjected to sonication for 5 minutes in Freon 113, the spectra were again taken, measured with an energy resolution of 1.1 eV/channel. The ESCA analysis volume (x-ray spot size X sampling depth) for this was approximately 600 pica meters times 1000 pica meters times 0.01 pica meters. The amount of extractable oxygen is then determined by the difference in oxygen content of the two analyses.

Among other factors, it was unexpectedly discovered there is a relationship between the surface properties of the foam 50, the bonding of an adhesive to the foam 50, and the temperature of the adhesive when the adhesive and foam 50 are brought into intimate contact. Surprisingly, we discovered that when the foam 50 has a high concentration of aging modifier present, the adhesive should be at a sufficiently high temperature that allows the adhesive to be fluid enough to adequately coat the foam's surface. When the concentration of the aging modifier is low or, alternatively, adequately bonded to the foam's 50 surface, an adhesive readily bonds to the surface, even when the adhesive has a temperature of less than about 100° F. (38° C.).

Although not wishing to be bound by any theory, it is believed that the low molecular weight aging modifier interferes with the adhesive's contact with the foam's 50 surface, requiring the adhesive to "flow" over the foam's surface when the aging modifier is present above a certain amount.

The term "high concentration of aging modifier" means an amount of aging modifier such that the amount of extractable oxygen, as measured by ESCA above, is greater than about 3%. The term "low concentration of aging modifier" means an amount of aging modifier such that the amount of extractable oxygen as measured by ESCA is less than about 3%, and preferably less than about 1%.

The foam 50 may be made from any light weight polyolefin foam material having the above characteristic and having two or more surfaces capable of being adhesively coated. Such foams may be a closed cell, crosslinked or a non-crosslinked polyolefin foam. Desirably, the foam 50 is a polypropylene or a polyethylene foam, with polyethylene being preferred. Particularly preferred is a non-crosslinked polyethylene foam.

The foam 50 must be flexible and capable of being formed into sheets. The foam 50 should have a thickness, as measured by ASTM D3575, ranging from about 0.015 of an inch (0.381 millimeters) to about 0.25 of an inch (6.35 millimeters). Preferably the foam 50 will have a thickness ranging from about 0.51 millimeters to about 1.54 millimeters, more preferably from about 0.76 millimeters to about 1.27 millimeters, and most preferably 0.76 millimeters to about 1.02 millimeters.

The foam 50 should have a density, also measured by ASTM D3575, ranging from about 1.4 lbs./ft$^3$ (0.0225 gm/cm$^3$) to about 6.0 lbs./ft$^3$ (0.0962 gm/cm$^3$), preferably ranging from about 2.0 lbs./ft$^3$ (0.0322 gm/cm$^3$) to about 4.0 lbs./ft$^3$ (0.0642 gm/cm$^3$), and most preferably from about 2.2 lbs./ft$^3$ (0.0354 gm/cm$^3$) to about 3.0 lbs./ft$^3$ (0.0482 gm/cm$^3$).

The foam's 50 thickness and density should be measured just after extrusion, prior to any cellular compaction that may occur through subsequent handling, packaging, or other methods or processes that may alter the foam's 50 characteristics. Examples of commercially available foams contemplated for use in the present invention include the trade name CA-30 foam manufactured by Sealed Air Corp. located at 19-01 State Highway 208; Fair Lawn, N.J. and trade name AF-030 manufactured by Astro-Valcour, Inc. located at 18 Peck Ave.; Glens Falls, N.Y.

Methods of producing a foam are well known in the foaming arts and are documented in the literature. For example *Cellular Solids*, L. J. Gibson and M. F. Ashby, Pergamon Press, 1988; and *Plastic Foams*, C. J. Benning, Wiley-Interscience, Volume 1, 1969 describe methods for making foams.

A garment adhesive can be any pressure-sensitive adhesive capable of adhering securely to a surface of the foam 50 and yet be releasable from the peel strip 80. For convenience, it is generally preferred to employ one of the hot melt adhesives already utilized by the manufacturer in the construction of the particular absorbent article. Representative of suitable adhesives are those hot melt adhesive compositions based on ethylene/vinyl acetate copolymers, isotactic or atactic polypropylene, styrene-butadiene, styrene-isoprene, or styrene-ethylene-butylene A-B-A or A-B-A-B block copolymers. Such adhesives are sold under the Kraton ®, Solprene ® and Stereon ® trade names. In addition to a base polymer, the hot melt adhesive is composed of tackifiers, oils and/or waxes as well as conventional additives including stabilizers, anti-oxidants, pigments and the like. Table I is exemplary of the range of adhesive viscosities that will work with this invention.

TABLE I

| Foam Type | Extractable Oxygen | Adhesive | Adhesive Temperature | Viscosity |
|---|---|---|---|---|
| Polypropylene | 0.7% | 34-2823 National Starch | ~90° F. | 8 × (10$^8$)cps |
| Polyethylene | >10 | 34-2823 National Starch | 165° F. | 6.8 × (10$^6$)cps |
| Polyethylene | >10 | 34-2823 National Starch | 190° F. | 1.79 × (10$^6$)cps |
| Polyethylene | >10 | 34-2823 National Starch | 275° F. | 4.9 × (10$^4$)cps |

A garment adhesive may be applied to the peel strip 80 by suitable methods known in the art, such as slot coating or spraying. Desirably, the adhesive has a thickness of at least 0.0001 of an inch (0.00254 millimeters), and preferably from about 0.0002 (0.0051 millimeters) to about 0.001 of an inch (00254 millimeters). The amount of adhesive ranges from about 12 gsm to about 40 gsm, preferably the amount ranges from about 18 gsm to about 30 gsm, and most preferably from about 18 gsm to about 25 gsm. It should be recognized that even though this amount of adhesive is adequate to anchor the foam 50 used in the panty liner 100, greater amounts of adhesive may be required for anchoring particular structures.

The peel strip 80 can be any suitable film-like material that does not adhere too tenaciously to a garment adhesive. Particularly preferred is a semi-bleached Kraft paper, one side of which is silicone coated to provide for easy release of the peel strip 80 from the adhesive.

Referring to FIG. 2, an alternative configuration for an assembly line for producing disposable absorbent articles using an adhesive heating means is shown. A liquid-pervious cover 110 has a thin, uniform layer of absorbent 130 air-laid onto one surface thereof. The cover 110 and the absorbent 130 are pressed between two rollers 140 and 145 to densify the absorbent 130. Optionally, the rollers 140 and 145 may supply sufficient pressure, and heat if required, to hydrogen bond the cover 110 to the absorbent 130 as well as to emboss a pattern thereon. A foam 150 is unwound from a supply roll 160 and sprayed with a hot melt construction adhesive 165 from sprayer 170. The foam 150 is then applied to the absorbent 130. Applicator 175 applies a garment adhesive 177 onto one surface of peel strip 180. The adhesive 177 is heated by a heating means 190 so that when the adhesive 177 contacts the foam 150 the adhesive 177 will be properly melted to permit bonding to the foam 150. Although not necessary, bonding of the garment adhesive 177 may be enhanced by one or more compression rollers 195, 196 and 197. After bonding, the laminate comprising: the cover 110, the absorbent 130, the foam 150, the adhesive 177 and the peel strip 180, is die cut into the panty liner 200 and packaged for shipment.

The materials employed for use as a cover 110, absorbent 130, spray adhesive 160 and garment adhesive 177 are as described above. The foam 150 employed as a backing deviates from the above description only in that it can have elevated levels of aging modifier. The term "elevated" means amounts of aging modifier greater than about 3%, determined as described above.

The heating means 190 supplies sufficient heat to the surface of the adhesive 177 so that when the adhesive 177 and foam 150 come into contact, the adhesive 177 has a temperature of from about 140° F. (60° C.) to about 330° F. (165.5° C.). Preferably the temperature is from about 160° F. (71° C.) to about 330° F. (165.5° C.), and most preferably from about 180° F. (82° C.) to about 220° F. (104° C.). Heating means are well known in the art and include, for example, blowing hot air and/or applying radiant heat normal to the adhesive 177 surface, the peel strip 180 surface, or combinations of both. Alternatively, rollers 195 and/or 196 can be utilized as a means for heating the adhesive. This preferred embodiment applies an advantageous directional force to the peel strip 180, adhesive 177, and foam 150 for enhancing the adhesive 177 bonding to the foam's 150 surface. It is also contemplated that the adhesive 177 be heated using any combination thereof.

The modes of using the panty liner 200 and performance characteristics of all embodiments of this invention disclosed herein are similar. While the panty liner may be used in its basic form, it is preferred that in preparing the panty liner 200 for use the peel strip 180 is removed from the pant liner 200, exposing the garment attachment adhesive 177. The panty liner is then centered and mounted in the crotch portion of an undergarment in the usual way.

Panty liners constructed in accordance with the present invention have been found to possess a high liquid absorption capacity. In addition, the panty liner is thin, soft and flexible so it is comfortable to the wearer. Another advantage is that the panty liner is resilient and conforms well to the surface of the body to which it is applied to achieve good gasketing effects. Yet another advantage is that the garment adhesive does not delaminate from the foam baffle upon removal of the peel strip or the panty liner from the undergarment.

While the invention has been described in conjunction with two specific embodiments, it is to be understood that many alternatives, modifications and variations will be apparent to those skilled in the art in light of the foregoing description. For example, a wide variety of absorbent products in which an absorbent core is bonded to an adjoining layer can incorporate the invention, including baby diapers, adult incontinent garments, training pants, wound dressing, sanitary napkins, and the like. Accordingly, this invention is intended to embrace all such modifications and variations which fall within the spirit and scope of the appended claims

We claim:

1. A method of bonding a garment adhesive to a closed-cell, non-crosslinked, liquid-impermeable, polyolefinic foam layer, said foam having less than about 3% aging modifier, as measured by an amount of extractable oxygen, said method comprising:
   (a) applying said garment adhesive to a surface of a substrate; and
   (b) bringing said adhesive surface of said substrate into contact with said polyolefinic foam, wherein said adhesive has a viscosity of less than about $8 \times 10^8$ centipoise.

2. The method of claim 1 wherein said polyolefin is polypropylene.

3. The method of claim 1 wherein said polyolefin is polyethylene.

4. The method of claim 1 wherein said substrate is suitable for use as a peel strip.

5. The method of claim 1 wherein said foam has less than about 1% aging modifier.

6. The method of claim 1 wherein said bonding is accomplished by concurrently compressing said substrate and said foam.

7. The method of claim 6 wherein said compressing is accomplished by means of a plurality of compression rollers.

8. The method of claim 1 wherein said foam has a thickness ranging from about 0.51 millimeters to about 1.54 millimeters and has a density ranging from about 0.0225 gm/cm$^3$ to about 0.0962 gm/cm$^3$.

9. The method of claim 8 wherein said foam has a thickness ranging from about 0.76 millimeters to about 1.27 millimeters and has a density ranging from about 0.0322 gm/cm$^3$ to about 0.0642 gm/cm$^3$.

10. The method of claim 9 wherein said foam has a thickness ranging from about 0.76 millimeters to about 1.02 millimeters and has a density ranging from about 0.0354 gm/cm$^3$ to about 0.0482 gm/cm$^3$.

11. A method of bonding a garment adhesive to a closed-cell, non-crosslinked, liquid-impermeable, polyolefinic foam baffle in an absorbent article, said method comprising:
   (a) applying said adhesive to a surface of a substrate;
   (b) brining said adhesive surface of said substrate into contact with said foam baffle bringing said adhesive surface of said substrate into contact with said foam baffle, said foam having a density ranging from about 0.0225 gm/cm$^3$ to about 0.0962 gm/cm$^3$; and
   (c) heating said adhesive to a temperature ranging from about 140° F. (60° C.) to about 330° F. (165.5° C.).

12. The method of claim 11 wherein said adhesive is heated to a temperature ranging from about 160° F. (71° C.) to about 330° F. (165.5° C.).

13. The method of claim 11 wherein said foam is a polyolefin foam.

14. The method of claim 13 wherein said polyolefin is polypropylene.

15. The method of claim 13 wherein said polyolefin is polyethylene.

16. The method of claim 15 wherein said adhesive is heated to a temperature ranging from about 180° F. (82° C.) to about 220° F. (104° C.).

17. The method of claim 11 wherein said substrate is suitable for use as a peel strip.

18. The method of claim 11 wherein said bonding is accomplished by concurrently compressing said substrate and said foam.

19. The method of claim 18 wherein said compressing is accomplished by means of a plurality of compression rollers.

20. The method of claim 11 wherein said foam has a thickness ranging from about 0.51 millimeters to about 1.54 millimeters.

21. The method of claim 11 wherein said foam has a thickness ranging from about 0.76 millimeters to about 1.27 millimeters and has a density ranging from about 0.0322 gm/cm$^3$ to about 0.0642 gm/cm$^3$.

22. The method of claim 11 wherein said foam has a thickness ranging from about 0.76 millimeters to about 1.02 millimeters and has a density ranging from about 0.0354 gm/cm$^3$ to about 0.0482 gm/cm$^3$.

23. The method of claim 11 wherein said adhesive is heated to a temperature ranging from about 180° F. (82° C.) to about 220° F. (104° C.).

* * * * *

UNITED STATES PATENT AND TRADEMARK OFFICE
CERTIFICATE OF CORRECTION

PATENT NO. : 5,360,504
DATED : November 1, 1994
INVENTOR(S) : Joseph P. Fell, Richard D. Schulz, Mary J. Meyer, Allan J. Krueger, Franklin M.C. Chen, and Yung H. Huang It is certified that error appears in the above-indentified patent and that said Letters Patent is hereby corrected as shown below:

Column 8, line 25, claim 11, (b) should read as follows:

(b) bringing said adhesive surface of said substrate into contact with said foam baffle, said foam having a density ranging from about 0.0225 $gm/cm^3$ to about 0.0962 $gm/cm^3$; and Signed and Sealed this Twenty-first Day of March, 1995

Attest:

BRUCE LEHMAN

*Attesting Officer*    *Commissioner of Patents and Trademarks*